United States Patent
Vandoni et al.

(10) Patent No.: US 7,879,901 B2
(45) Date of Patent: Feb. 1, 2011

(54) SUBLINGUAL FORMULATIONS OF KETOROLAC OR SALTS THEREOF

(75) Inventors: Guido Vandoni, Correzzana (IT); Carlo Oliani, Hortolandia (BR); Adriano Coelho, Hortolandia (BR); Heny Zaniboni, Hortolandia (BR)

(73) Assignee: Nature's Plus Farmaceutica Ltda., Hortolandia, SP (BR)

( * ) Notice: Subject to any disclaimer, the term of this patent is extended or adjusted under 35 U.S.C. 154(b) by 986 days.

(21) Appl. No.: 10/559,252

(22) PCT Filed: May 26, 2004

(86) PCT No.: PCT/BR2004/000077

§ 371 (c)(1),
(2), (4) Date: Dec. 2, 2005

(87) PCT Pub. No.: WO2004/105678

PCT Pub. Date: Dec. 9, 2004

(65) Prior Publication Data

US 2006/0128782 A1 Jun. 15, 2006

(30) Foreign Application Priority Data

Jun. 2, 2003 (BR) .................... 0302736

(51) Int. Cl.
*A61K 31/407* (2006.01)
*A61K 31/7016* (2006.01)
*A61K 31/047* (2006.01)
*A61K 31/717* (2006.01)
*A61K 9/00* (2006.01)
*A61K 9/34* (2006.01)

(52) U.S. Cl. .................. 514/412; 514/960; 514/781; 514/775; 514/777

(58) Field of Classification Search .......... 514/412, 514/960, 781, 775, 777
See application file for complete search history.

(56) References Cited

U.S. PATENT DOCUMENTS

| 4,089,969 | A | 5/1978 | Muchowski et al. |
| 5,288,497 | A | 2/1994 | Stanley et al. |
| 5,626,838 | A | 5/1997 | Cavanaugh, Jr. |
| 6,090,368 | A | 7/2000 | Zia et al. |
| 6,685,951 | B2 | 2/2004 | Cutler |
| 2002/0071857 | A1* | 6/2002 | Kararli et al. ........ 424/435 |
| 2003/0235617 | A1* | 12/2003 | Martino et al. ........ 424/481 |

FOREIGN PATENT DOCUMENTS

| EA | 0674511 | A1 | 10/1995 |
| EP | 0668759 | A1 | 8/1995 |
| WO | WO-91/13609 | A1 | 9/1991 |
| WO | WO-96/28144 | A1 | 9/1996 |
| WO | WO-99/09954 | A1 | 3/1999 |

OTHER PUBLICATIONS

Drug Facts and Comparisons, 1994 edition, Wolters Kluwer Co. pp. 1228-1229.*
Drug Facts and Comparisons, 1994 edition, Wolters Kluwer Co. pp. 1228-1229.*
http://www.chemindustry.com/chemicals/1418620.html accessed Jan. 12, 2009.*

* cited by examiner

*Primary Examiner*—Andrew D Kosar
*Assistant Examiner*—Donna Jagoe
(74) *Attorney, Agent, or Firm*—Birch, Stewart, Kolasch, Birch, LLP

(57) ABSTRACT

The present invention refers to pharmaceutical compositions based on ketorolac or one of its salts pharmaceutically acceptable, as well as the use of ketorolac or one of its salts acceptable from pharmaceutical viewpoint, for preparation of a pharmaceutical composition (tablets) for sublingual administration, with the purpose of accelerating the pharmacological response to ketorolac, without making use of the injectable via. On the other hand, a pharmaceutical composition is described encompassing, as one of its active principles, ketorolac or one of its salts acceptable from pharmaceutical viewpoint, representing from 10 to 15% by weight, in relation to the total weight of the compound and as the essential excipient, a ternary mixture of lactose/sorbitol/cellulose, eventually in a mixture with other excipients acceptable from pharmaceutical viewpoint.

14 Claims, No Drawings

SUBLINGUAL FORMULATIONS OF KETOROLAC OR SALTS THEREOF

This Application is the National Phase Under 35 U.S.C. §371 of PCT International Application No. PCT/BR2004/000077 which has an International filing date of May 26, 2004, which claims priority to Brazilian Application No. PI0302736-8 filed on Jun. 2, 2003.

FIELD OF THE INVENTION

The present invention refers to the use of ketorolac or one of its pharmaceutically acceptable salts, for preparation of a pharmaceutical composition in tablets, for sublingual administration, to accelerate the pharmaceutical response, especially the analgesic response by the use of ketorolac.

STATE OF THE ART

Ketorolac is an inhibitor of prostaglandin synthesis, which formula is

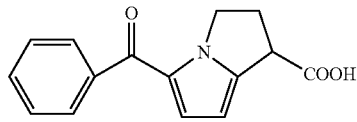

notably known by its anti-inflammatory, analgesic and antipyretic action as described in U.S. Pat. No. 4,089,969, in which tromethamol salt is used in its racemic form.

Pharmaceutical formulations with analgesic and antipyretic action, containing R form, were also described in the state of the art, as in the patent document EP 674511. It should also be emphasized that ketorolac may be used in periodontal affection treatments, as described in patent document WO 91/13609, and for the treatment of carcinomas of the scaly cells in the oral cavity or of the oropharynx, as taught in the patent document WO 96/28144.

In the several indications mentioned in the literature, ketorolac was proposed for use in several administration routes. For example, U.S. Pat. No. 4,089,969 suggests the oral, parenteral or topical administration, in several pharmaceutical forms, particularly in tablets, suppository, pills, capsules, powder, solutions, suspensions, emulsions, creams, lotions and unguents.

However, patent document WO 91/13609 suggests the application of ketorolac through dentifrices, solutions for mouthwash, spray for oral cavity or dental solutions. The latter type of ketorolac application is also suggested in patent document WO 96/28144.

The U.S. Pat. No. 6,090,368 describes the nasal spray, whereas patent document WO 99/09954 describes a compound for skin topic administration and patent document EP 668759 describes ketorolac by transdermal administration.

Currently, ketorolac, in the form of tromethanol salt is used for oral administration in tablets of 10 mg or dropwise, in a solution of 2%, administration by injection, being provided in flasks of 10 or 30 mg, and for rectal administration in suppositories of 30 mg.

Consequently, in order to obtain a rapid anti-inflammatory, antipyretic and analgesic action of ketorolac, the single current possibility is to use the injectable administration, which is known to cause slight illness and discomfort to the patient. Particularly due to its use as analgesic, a greater speed of ketorolac action assumes a significant importance.

SUMMARY OF THE INVENTION

It was recently proved that with administration of ketorolac or one of its pharmaceutically acceptable salts, in particular its tromethamol salt, absorption of the active ingredient is more rapid when the active ingredient is administered sublingually as compared to adsorbtion afteroral administration, thus resulting in a more rapid therapeutic action with plasmatic levels of the active principle equal or very close to those obtained after the traditional oral administration, which results in a therapeutic activity very close, equal to or even better than traditional oral administration.

On the other hand, it was proved that a pharmaceutical, composition comprising the essential carrier containing 10-15% in weight of ketorolac or one of its pharmaceutically acceptable salts, preferably tromethamol ketorolac, and with at least 60% of the total weight of the composition represented by essential excipients, composed by ternary mixture of lactose/sorbitol/cellulose in the respective weight percentages (in relation to the total weight of the composition) of 30-50%/3-9%/9-17%, is rapidly absorbed by sublingual administration, rapidly achieving hematic levels of ketorolac, at sufficient levels to assure the therapeutic activity desired in the above mentioned indications, particularly the analgesic property.

The term "essential carrier" refers to the pharmaceutical composition containing a mixture of the active principle of ketorolac compound or one of its pharmaceutically acceptable salts, particularly its tromethamol salt, an excipient necessary to compose the formulation, which is presented in the form of sublingual tablets for oral administration, including the essential excipients. The term "essential excipients" refers to the mixture of the excipients or the ternary mixture lactose/sorbitol/cellulose in specific proportions (lactose (30-50% in weight)/sorbitol (3-9% in weight)/cellulose (9-17% in weight). The term "ternary mixture" refers to the three excipients, lactose/sorbitol/cellulose. Hereinafter, the terms essential carrier, essential excipients and ternary mixture will appear in the present document meaning the foregoing explanation.

The term "ketorolac" represents the International Common Denomination" (DCI) of the racemic form of 5-benzyl-2,3-dihydro-1H-pyrrolizin-1-carboxylic acid.

The term "tromethamol" represents the DCI of 2-amino-2-(hydroxymethyl)-1,3-propanediol, also indicated as "tromethamine" in USP dictionary of pharmaceutical products.

The expression "tromethamol ketorolac", specifically designates the tromethamol ketorolac salt.

DETAILED DESCRIPTION OF THE INVENTION

According to one of its aspects, the present invention refers to the use of ketorolac or one of its pharmaceutically acceptable salts, for the preparation of a pharmaceutical composition for sublingual administration which accelerates the pharmacological response to ketorolac without using administration by injection. It is understood by the term "sublingual", the application of the active principle through the administration of the pharmaceutical composition in the said sublingual form, i.e., under the tongue or gingiva, i.e., placing the tablet between the cheek and the gingiva.

It is understood that the expression "pharmacological response to ketorolac" refers to the response due to the systemic action of ketorolac itself or one of its pharmaceutically acceptable salts, preferably the trometamol salt, in the treatment of the aforementioned diseases.

One of the advantageous uses of ketorolac or one of its pharmaceutically acceptable salts, consists of the preparation of a pharmaceutical composition for sublingual administration with the purpose of accelerating the analgesic response of ketorolac without using administration by injection. Even more advantageous, the invention refers to the use of tromethamol ketorolac for preparation of the pharmaceutical compounds for sublingual administration which accelerates the analgesic response of ketorolac without using admistration by injection.

According to one of its other aspects, the present invention provides a pharmaceutical composition for sublingual use, due to the quality of one of its principle actives, reaching from 10 to 15% in weight of ketorolac or one of its pharmaceutically acceptable salts, mixed with a pharmaceutical excipient formed by, at least, 60% in relation to the total weight of the excipients of a diluent composed of a polyalcohol derivative from reduction of a monosaccharide and a carbohydrate, at least.

In the present context, unless otherwise indicated, the specific indication of the percentages is given in weight and refers to the total weight of the composition.

The referred pharmaceutical composition may promote the acceleration of ketorolac pharmacological response. It is composed of tablets for sublingual administration containing from 2 to 15 mg of ketorolac or one of its pharmaceutically acceptable salts.

The composition of the invention is particularly useful to obtain the rapid induction of analgesia in patients requiring this rapid induction.

The recommended dosage unit of the inventive composition is composed of 2.5; 5 or 10 mg of ketorolac, preferably tromethamol ketorolac mixed with excipients, of which, at least, 60% is composed of a polyalcohol derivative of a monosaccharide and of, at least, a carbohydrate, and eventually, other excipients as lubricants, aggregate, sweetening, taste correctors (flavors) and casually, disaggregating agents used in the manufacture of pills and tablets for sublingual use.

Certain excipients are considered to be advantageous excipients or essential excipients. For instance, advantageous or essential excipients include excipients used in quantity of at least 60% in weight in relation to the total weight of the composition, the carbohydrates as cellulose powder, microcrystalline cellulose or sodium carboxy-methylcellulose, lactose, corn or potato starch, natural or modified, or mixtures thereof and polyalcohol derivatives from reduction of monosaccharides as D-mannitol, L-glucitol and especially, D-glucitol or sorbitol, which may also act as sweetening agent.

The inventive composition may also include other excipients. These other excipients include lubricants such as polyethyleneglycol, especially polyethylene-glycol 6000 used in quantities corresponding to 0-5% by weight, aggregatives such as microcrystalline silica are used with weight ranging between 0.5 and 5%, disaggregating agents such as polyvinyl pyrrolidone generally representing from 5 to 10% by weight. In practice, carbohydrates and derivatives thereof, essentially compose the excipients of the composition of the present invention.

Due to the sublingual use of the pharmaceutical preparation of the present invention, the sweeteners and/or the flavorings constitute an essential presence and will be chosen by experts of the area, in relation to the organoleptic characteristics of any of the active principles. The natural sweetening properties of certain ingredients are advantageously being used, including mannitol and sorbitol, which in this case are part of the diluents, the latter being used in quantities corresponding to 3-9%. Synthetic sweeteners such as sodium saccharine or aspartame are used in quantities of 0.1-5%.

Flavoring ingredients may also be added to the composition and may have flavors chosen from among synthetic or natural oils, encompassing plant, leaf, flower, fruit extracts and combinations thereof, such as cinnamon, *mentha piperita*, anise, cedar leaves, bitter almond, citrus fruits, especially orange and lemon, chamomile and grapefruit. Flavoring ingredients providing flavors such as vanilla or eucalyptus and fruit essences, especially apple, pear, peach, raspberry, cherry and grape may also be used.

Generally, the flavoring ingredients are present in quantities ranging from 0.05% to 4% of the total weight of the compound. The preferred flavors are the tropical flavors and those that give mint or fruit taste, particularly of grape, cherry or citric fruits, especially orange, lemon or mixtures thereof.

Another aspect of the present invention provides a pharmaceutical composition that comprises 10-15% by weight of ketorolac or one of its pharmaceutically acceptable salts, preferably from 60 to 75% of the total weight of the compound of an essential excipient, composed of a ternary mixture of lactose/sorbitol/cellulose, in the respective weight percentages (in relation to the total weight of the compound) of lactose 30-50%/sorbitol 3-9%/cellulose 9-17%, preferably of lactose 40-50%/sorbitol 5-8%/cellulose 12-14%. Preferably, in the referred to essential excipient, the ratio of lactose/cellulose is approximately 2.5/1 close to 3.5/1, and sorbitol represents 6-8% of the total weight of the compound. The referred to pharmaceutical composition is found in dosage units of, for example, tablets containing from 2 to 15 mg, preferably 2.5, 5 or 10 mg of ketorolac or one of its pharmaceutically acceptable salts, preferably tromethamol ketorolac. This type of tablets is especially appropriate for sublingual administration.

According to a preferential aspect of the invention, the referred to essential excipient is composed of a mixture of lactose (45-48% by weight)/sorbitol (5-8% by weight)/cellulose (12-15% by weight), the ratio of lactose/sorbitol/cellulose is lactose $3\pm0.5$/sorbitol $0.6\pm0.2$/cellulose 1 by weight eventually in a mixture with other excipients acceptable from pharmaceutical viewpoint.

The essential excipients, composed of the mixture lactose/sorbitol/cellulose in the referred to weight percentages, in relation to the total weight of the compound is preferably a mixture with a proportion of approximately lactose 3/sorbitol 0.4-0.7/cellulose 1, containing ternary mixture forming the essential excipients in the weight percentages, each one always referring to the total weight of the compound, lactose (30-50%)/sorbitol (3-9%)/cellulose (9-17%).

The referred to composition is particularly indicated for sublingual administration.

In addition to the essential excipients, lactose/sorbitol/cellulose, the composition of the invention may contain other excipients, especially disaggregating agents, as polyvinyl pyrrolidone, corn or potato starch, eventually modified, lubricants as magnesium stearate, aggregative agents, as methylcellulose, sodium carboxymethylcellulose, polyethyleneglycol, silica microcrystalline, colloidal silicon dioxide, magnesium and aluminum silicate, dyers as titanium dioxide, sweetening and flavors as previously mentioned.

The composition of the present invention may contain excipients that give it effervescence during its administration under the tongue. Effervescent excipients may include mixtures of acids and carbonates, adequately prepared in accordance with the usual techniques, especially citric or tartaric acid and sodium, potassium or magnesium carbonate or bicarbonate.

The tablets for sublingual administration of the present invention may be manufactured in accordance with the classic methods used in pharmaceutical technique, for example, by direct compression, by humid granulation or using technology of active principle incorporation in micro-granules, microsphere or micro-emulsions, allowing better absorption of the referred to active principle.

The composition of the present invention will be prepared according to methods of pharmaceutical technique.

In practice, the calculated quantity of tromethamol ketorolac, of sorbitol, (preferably micro-granulated) and one aggregative, for example, sodium carboxymethyl-cellulose, will pass through a sieve and be mixed for 10-15 minutes. To this mixture will be added the calculated quantity of lactose and cellulose, (preferably micronized), and a disaggregate such as polyvinyl pyrrolidone or crospovidone, for example, Polyplasdone XL, of a ligand as colloidal silicon, for example, Syloid 244, and a flavoring ingredient and a sweetener. Then, all these excipients are passed through a sieve of 30 mesh and mixed for an additional 10-15 minutes. To the mixture thus obtained the calculated quantity of a lubricant will be added. The lubricant may be, for example, magnesium stearate or polyethyleneglycol. After adding the lubricant the composition is further mixed for some minutes and then the mixture is compressed with appropriate punctures.

The composition of the present invention, with the administration of a dose of 10 mg, rapidly achieves hematic rates of ketorolac upon administration, thus ensuring rapid analgesic or anti-inflammatory action.

The bioavailability after sublingual administration of a single dose of 10 mg of tromethamol ketorolac was compared with the same single dose of the active ingredient in conventional oral tablets, in a study with twelve healthy male volunteers recruited after the respective information on the nature and characteristics of the active principles and also on the scope of the study.

This study, composed of four treatment periods, was carried out according to a crossed and randomized scheme.

All individuals received the pre-established dose of the active principle in the form of conventional oral tablets, in the form of sublingual tablets, by endovenous and intramuscular administration, with a washout period of at least seven days after the first treatment and each subsequent treatment, according to a pre-established list of randomization. The sublingual tablets were placed under the tongue in relation to the venous plexus, and kept there until its complete dissolution, whereas the conventional oral tablets were swallowed unbroken with 150 ml of mineral water. Five ml of venous blood were collected in the periods 0-5-10-20-40 minutes, 1-2-4-8 and 24 hours after the treatment. Table I shows the average plasmatic rates measured after the single doses mentioned.

In the above table, in the first minutes after the sublingual administration, there is a tendency for obtaining hematic rates higher in relation to those obtained after administration of the same dose by oral or intramuscular administration, whereas the plasmatic rates achieved by endovenous administration are easily overcome.

Table II shows the data referring to the several pharmacokinetic parameters (average±standard deviation) referring to sublingual, conventional oral, endovenous and intramuscular administration of tromethanol ketorolac. Especially the $AUC_{0-t}$ informed in the Table, i.e., the area under the time curve 0 up to time T (in this case, at hour 24), its logarithm $AUC_{0-inf}$ (in ng/ml/h) i.e., the area under the curve according to the formula $$AUC_{o\text{-}inf} = AUC_{0\text{-}t} + C_{t/b}$$

in which $C_t$ is the plasmatic concentration (in ng/ml) estimated at time T (in this case, at hour 24) and b is the slope of the curve of the washout phase, being its logarithm, the $C_{max}$ (in ng/ml), i.e., the peak of maximum concentration, its logarithm and the $T_{max}$, i.e., the time (in hours) in which the maximum plasmatic concentration peak is compared.

TABLE II

| PHARMACO-KINETIC PARAMETERS | Sublingual Tablets | Conventional Tablets | E.V. | I.M. |
|---|---|---|---|---|
| $AUC_{0\text{-}t}$ (ng/ml/h) | 237972.81 ± 141094.58 | 233989.13 ± 118781.73 | 260432.85 ± 141307.54 | 260002.03 ± 96077.99 |
| $AUC_{0\text{-}inf}$ (ng/ml/h) | 258205.10 ± 143740.06 | 263791.13 ± 124504.49 | 281323.89 ± 140122.03 | 278349.95 ± 92737.20 |
| Log $AUC_{0\text{-}t}$ | 5.30 ± 0.28 | 5.31 ± 0.24 | 5.36 ± 0.22 | 5.38 ± 0.22 |
| Log $AUC_{0\text{-}inf}$ | 5.34 ± 0.27 | 5.37 ± 0.24 | 5.40 ± 0.21 | 5.41 ± 0.19 |
| $C_{max}$ (ng/ml) | 991.47 ± 219.40 | 871.28 ± 236.90 | 2858.89 ± 680.35 | 835.31 ± 196.13 |
| Log $C_{max}$ | 2.99 ± 0.10 | 2.92 ± 0.13 | 3.45 ± 0.10 | 2.91 ± 0.11 |
| $T_{max}$ (min) | 33.33 ± 13.03 | 53.33 ± 9.85 | 10 — | 51.67 ± 10.30 |

From the statistic analyses made from all pharmacokinetic parameters, using the analysis of variance (ANOVA) and the test of Bonferroni, and also only on the $T_{max}$ parameter, the tests for the data in pairs of Wilcoxon, did not result in significant differences in the treatments with reference to logAUC$_{o\text{-}inf}$, either in ANOVA test or in Bonferroni test, while a significant difference can be observed between the endovenous treatment and the other ways of administration with reference to logC$_{max}$. With reference to $T_{max}$ parameter, it was observed that either in ANOVA test or in Bonferroni

TABLE I

| | 0 | 5 minutes | 10 minutes | 20 minutes | 40 minutes | 1 hour | 2 hours | 4 hours | 8 hours | 24 hours |
|---|---|---|---|---|---|---|---|---|---|---|
| E.V. | 0 | 315.83 ± 136.09 | 2858.89 ± 680.35 | 1096.58 ± 376.46 | 794.31 ± 274.46 | 637.20 ± 243.46 | 504.58 ± 228.98 | 332.41 ± 177.30 | 156.80 ± 83.02 | 16.21 ± 18.04 |
| I.M. | 0 | 5.70 ± 10.39 | 119.09 ± 56.83 | 245.20 ± 115.17 | 543.08 ± 316.31 | 720.04 ± 201.80 | 448.85 ± 117.88 | 323.04 ± 103.29 | 193.88 ± 63.74 | 25.63 ± 19.82 |
| Conventional Tablet | 0 | 0 | 43.73 ± 42.88 | 227.15 ± 73.17 | 660.69 ± 303.43 | 730.60 ± 235.35 | 480.28 ± 232.68 | 317.03 ± 190.96 | 161.04 ± 87.83 | 26.29 ± 22.94 |
| Sublingual Tablet | 0 | 43.28 ± 31.81 | 205.26 ± 95.16 | 736.30 ± 275.13 | 776.26 ± 287.80 | 626.88 ± 260.98 | 429.04 ± 212.33 | 305.71 ± 182.59 | 158.35 ± 97.70 | 25.41 ± 25.46 | and Wilcoxon tests, there is a significant difference between the treatment by sublingual administration and those by conventional oral or intramuscular administration. It was especially evidenced that the sublingual treatment presents a $T_{max}$ significantly shorter in relation to the conventional oral or intramuscular treatment, considered equal between it.

The following examples explain the invention, however, without limiting the same.

Example 1

A mixture of 1.000 kg of tromethamol ketorolac, 0.500 kg of micro-granulated sorbitol and 0.200 kg of sodium carboxymethylcellulose is passed through a sieve of 30 mesh, and after that, mixed for 10 minutes. Add to this mixture, 3.375 kg of lactose, 1.125 kg of micronized cellulose, 0.150 kg of sodium saccharine, 0.6 kg of Polyplasdone XL, 0.100 kg of Syloid 244 and 0.250 kg of lemon flavor, previously passed through a sieve of 30 mesh. Slurry the mixture for 10 minutes. Add 0.200 kg of magnesium stearate previously passed through a sieve of 30 mesh. Slurry the end-mixture for 3 minutes. Promote the compression in an alternative or rotating compression machine, provided with punctures with 6 mm diameter. Thus, 100,000 tablets will be obtained with a weight of 75 mg each, with a formulation showing the following composition:

| | |
|---|---|
| Tromethamol Ketorolac | 10.00 mg |
| Lactose | 33.75 mg |
| Sorbitol | 5.00 mg |
| Micronized Cellulose | 11.25 mg |
| Sodium Carboxymethylcellulose | 2.00 mg |
| Sodium Saccharine | 1.50 mg |
| Polyplasdone XL | 6.00 mg |
| Syloid 244 | 1.00 mg |
| Lemon flavor | 2.50 mg |
| Magnesium stearate | 2.00 mg |

The tromethamol ketorolac tablets for sublingual administration thus obtained, contain 13.33% of active principle and 66.67% of essential excipients, among which lactose represents 45% of the total compound, sorbitol representing 6.67% of the total compound and cellulose representing 15% of the total compound, being the proportion of lactose/sorbitol/cellulose of 3/0.44/1.

Example 2

Carrying out the same operation described in Example 1 above, with 1.000 kg of tromethamol ketorolac, 4.500 kg of Cellactose, composed of a mixture containing 75% of lactose and 15% of cellulose, 0.500 kg of micro-granulated sorbitol, 0.200 kg of sodium carboxymethyl-cellulose, 0.600 kg of polyvinyl pyrrolidone (Collidon Cl BASF), 0.250 kg of lemon flavor (15203-71/MD-Givaudan), 0.100 kg of microcrystalline silica (Syloid 244), 0.200 kg of magnesium stearate and 0.150 kg of sodium saccharine 100,000 tablets will be prepared with a weight of 75 mg each, presenting the following composition:

| | |
|---|---|
| Tromethamol Ketorolac | 10.00 mg |
| Lactose | 33.75 mg |
| Microcrystalline Cellulose | 11.25 mg |
| Microgranulated Sorbitol | 5.00 mg |
| Polyvinyl pyrrolidone | 6.00 mg |
| Sodium Carboxymethylcellulose | 2.00 mg |
| Lemon flavor | 2.50 mg |
| Sodium Saccharine | 1.50 mg |
| Magnesium stearate | 2.00 mg |
| Microcrystalline Silica | 1.00 mg |

The tromethamol ketorolac tablets for sublingual administration thus obtained contain 13.33% of active principle and 66.67% of essential excipients, among which lactose represents 45% of the total compound, sorbitol representing 6.67% of the total compound and cellulose representing 15% of the total compound, being 3/0.44/1 the respective proportion of lactose/sorbitol/cellulose.

The invention claimed is:

1. A pharmaceutical composition, for sublingual use, comprising an active ingredient and essential excipients, said active ingredient consisting of from 10 to 15% by weight of ketorolac or one of its pharmaceutically acceptable salts and, at least 60% of essential excipients, wherein said essential excipients comprise a mixture of lactose/sorbitol/cellulose with the respective weight percentages of 30-50%/3-9%/9-17% in the total composition.

2. The pharmaceutical composition according to claim 1, wherein said essential excipient represents 60-75% of the total weight of the composition.

3. The pharmaceutical composition according to claim 1, wherein said essential excipient is composed of a mixture of 45-48% lactose, 6-8% sorbitol and 12-15% cellulose.

4. The pharmaceutical composition according to claim 1, wherein the mixture lactose/cellulose of said essential excipient, is in the proportion of lactose/cellulose of 2.5/1 up to 3.5/1 by weight, and sorbitol represents 6-8% of the total weight of the composition.

5. The pharmaceutical composition according to claim 1, wherein in said essential excipient, the proportion lactose/sorbitol/cellulose is 3±0.5/0.6±0.2/1 by weight.

6. The pharmaceutical composition according to claim 1, wherein in said essential excipient, the proportion lactose/sorbitol/cellulose is 3/0.4-0.7/1 by weight.

7. The pharmaceutical composition according to claim 1, wherein the active ingredient consists of from 2 to 15 mg of ketorolac or one of its pharmaceutically acceptable salts.

8. The pharmaceutical composition according to claim 7, wherein said pharmaceutically acceptable salt is tromethamol salt.

9. The pharmaceutical composition according to claim 8, wherein said active ingredient consists of 2.5 mg of ketorolac tromethamol.

10. The pharmaceutical composition according to claim 8, wherein said active ingredient consists of 5 mg of ketorolac tromethamol.

11. The pharmaceutical composition according to claim 8, wherein said active ingredient consists of 10 mg of ketorolac tromethamol.

12. The pharmaceutical composition according to claim 7, wherein in said essential excipient, the proportion lactose/sorbitol/cellulose is 2.5-3.5/0.4-0.8/1 by weight in mixture with other excipients.

13. The pharmaceutical composition according to claim 1, which is formulated for sublingual administration which accelerates the pharmacological response to ketorolac, wherein said active ingredient consists of 2 to 15 mg of ketorolac or one of its pharmaceutically acceptable salts, and wherein said active ingredient is mixed with at least 60% of said essential excipient consisting of a ternary mixture of lactose/sorbitol/cellulose in the respective percentages in weight of 30-50%/3-9%/9-17% of the total weight of the composition.

14. A method of administering ketorolac or one of its pharmaceutically acceptable salts comprising administering the composition of claim 1 by sublingual administration thereby accelerating the pharmacological responses to ketorolac.

* * * * *